(12) United States Patent
Basu et al.

(10) Patent No.: US 10,631,928 B2
(45) Date of Patent: Apr. 28, 2020

(54) CATHETER WITH DEFORMABLE DISTAL ELECTRODE

(71) Applicant: BIOSENSE WEBSTER (ISRAEL) LTD., Yokneam (IL)

(72) Inventors: Shubhayu Basu, Anaheim, CA (US); Mario A. Solis, Rancho Cucamonga, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 216 days.

(21) Appl. No.: 15/469,252

(22) Filed: Mar. 24, 2017

(65) Prior Publication Data

US 2018/0271590 A1    Sep. 27, 2018

(51) Int. Cl.
*A61B 18/14*    (2006.01)
*A61M 25/00*    (2006.01)
(Continued)

(52) U.S. Cl.
CPC ....... *A61B 18/1492* (2013.01); *A61M 25/008* (2013.01); *A61M 25/0043* (2013.01);
(Continued)

(58) Field of Classification Search
CPC ............ A61M 25/0043; A61M 25/008; A61M 2025/0081; A61M 2205/0216;
(Continued)

(56) References Cited

U.S. PATENT DOCUMENTS 5,341,807 A    8/1994    Nardella
5,391,199 A    2/1995    Ben-Haim
(Continued)

FOREIGN PATENT DOCUMENTS

CN    1867299 A    11/2006
EP    1 679 034 A1    7/2006
(Continued)

OTHER PUBLICATIONS

U.S. Appl. No. 61/718,981, filed Oct. 26, 2012, 11 pages.
(Continued)

*Primary Examiner* — Jaymi E Della
*Assistant Examiner* — Rachel A. Vierra
(74) *Attorney, Agent, or Firm* — Lewis Roca Rothgerber Christie LLP

(57) ABSTRACT

A catheter probe configured with a capability to present a larger tissue contact area or "footprint" for larger, deeper lesions, without increasing the french size of the catheter, especially its distal section, includes an elastically deformable electrode configured to adopt a neutral configuration and a tissue contact configuration. The deformable electrode comprising a hollow porous tube with a distal portion having a closed distal end, and a proximal portion defining an opening to an interior of the tube, where the distal tip end is received in the tube through the opening and the distal section is generally surrounded by tube, with the proximal portion being affixed to an outer surface of the distal section. In some embodiments, the closed distal end is shaped with a bulbous portion that can spread and widen to provide a larger surface contact area.

16 Claims, 8 Drawing Sheets

(51) Int. Cl.
  *A61B 18/00* (2006.01)
  *A61B 90/00* (2016.01)
  *A61B 34/20* (2016.01)

(52) U.S. Cl.
  CPC ....... *A61B 90/37* (2016.02); *A61B 2018/0022* (2013.01); *A61B 2018/00023* (2013.01); *A61B 2018/00065* (2013.01); *A61B 2018/00077* (2013.01); *A61B 2018/00267* (2013.01); *A61B 2018/00351* (2013.01); *A61B 2018/00357* (2013.01); *A61B 2018/00577* (2013.01); *A61B 2018/00714* (2013.01); *A61B 2018/00744* (2013.01); *A61B 2018/00988* (2013.01); *A61B 2018/1465* (2013.01); *A61B 2034/2051* (2016.02); *A61B 2090/064* (2016.02); *A61B 2090/067* (2016.02); *A61B 2090/3958* (2016.02); *A61B 2218/002* (2013.01); *A61M 2205/0216* (2013.01); *A61M 2205/0233* (2013.01)

(58) Field of Classification Search
  CPC ...... A61M 2205/0233; A61M 25/0069; A61B 2018/00065; A61B 2018/00071; A61B 18/1492; A61B 2018/00023; A61B 2018/00077; A61B 2018/0022; A61B 2018/00267; A61B 2018/00351; A61B 2018/00357; A61B 2018/00577; A61B 2018/00714; A61B 2018/00744; A61B 2018/00988; A61B 2018/1465; A61B 2034/2046; A61B 2034/2051; A61B 2090/064; A61B 2090/067; A61B 2090/3958; A61B 2218/002; A61B 90/37
  See application file for complete search history.

(56) References Cited

U.S. PATENT DOCUMENTS

| | | |
|---|---|---|
| 5,443,489 A | 8/1995 | Ben-Haim |
| 5,471,982 A | 12/1995 | Edwards et al. |
| 5,558,091 A | 9/1996 | Acker et al. |
| 5,595,183 A | 1/1997 | Swanson et al. |
| 5,643,197 A | 7/1997 | Brucker et al. |
| 5,720,719 A | 2/1998 | Edwards et al. |
| 5,720,810 A | 2/1998 | Arai et al. |
| 5,846,238 A | 12/1998 | Jackson et al. |
| 5,944,022 A | 8/1999 | Nardella et al. |
| 5,983,126 A | 11/1999 | Wittkampf |
| 6,172,499 B1 | 1/2001 | Ashe |
| 6,177,792 B1 | 1/2001 | Govari et al. |
| 6,456,864 B1 | 9/2002 | Swanson et al. |
| 6,690,963 B2 | 2/2004 | Ben-Haim et al. |
| 6,788,967 B2 | 9/2004 | Ben-Haim et al. |
| 6,923,805 B1 | 8/2005 | LaFontaine et al. |
| 8,249,685 B2 | 8/2012 | Falwell et al. |
| 8,357,152 B2 | 1/2013 | Govari et al. |
| 9,289,141 B2 | 3/2016 | Lowery et al. |
| 2005/0096647 A1 | 5/2005 | Steinke |
| 2006/0004353 A1 | 1/2006 | Koyfman et al. |
| 2007/0106290 A1 | 5/2007 | Turano et al. |
| 2007/0156138 A1 | 7/2007 | Eisele |
| 2009/0043301 A1 | 2/2009 | Jarrard et al. |
| 2011/0130648 A1 | 6/2011 | Beeckler et al. |
| 2014/0121657 A1 | 5/2014 | Bar-Tal |
| 2014/0236146 A1* | 8/2014 | McLawhorn .......... A61B 18/14 606/41 |
| 2015/0038960 A1* | 2/2015 | Gunday ........... A61B 17/32072 606/34 |
| 2015/0351652 A1* | 12/2015 | Marecki ............... A61B 5/6856 600/374 |
| 2017/0333125 A1* | 11/2017 | Lepak ................. A61B 1/0684 |

FOREIGN PATENT DOCUMENTS

| | | |
|---|---|---|
| WO | WO 97/25917 | 7/1997 |
| WO | WO 2007/055783 A1 | 5/2007 |

OTHER PUBLICATIONS

Drawings for U.S. Appl. No. 61/718,981, filed Oct. 26, 2012, 6 pages.
English translation of CN Office action dated Dec. 4, 2017, issued in CN Application No. 201310512224.6, 10 pages.

* cited by examiner

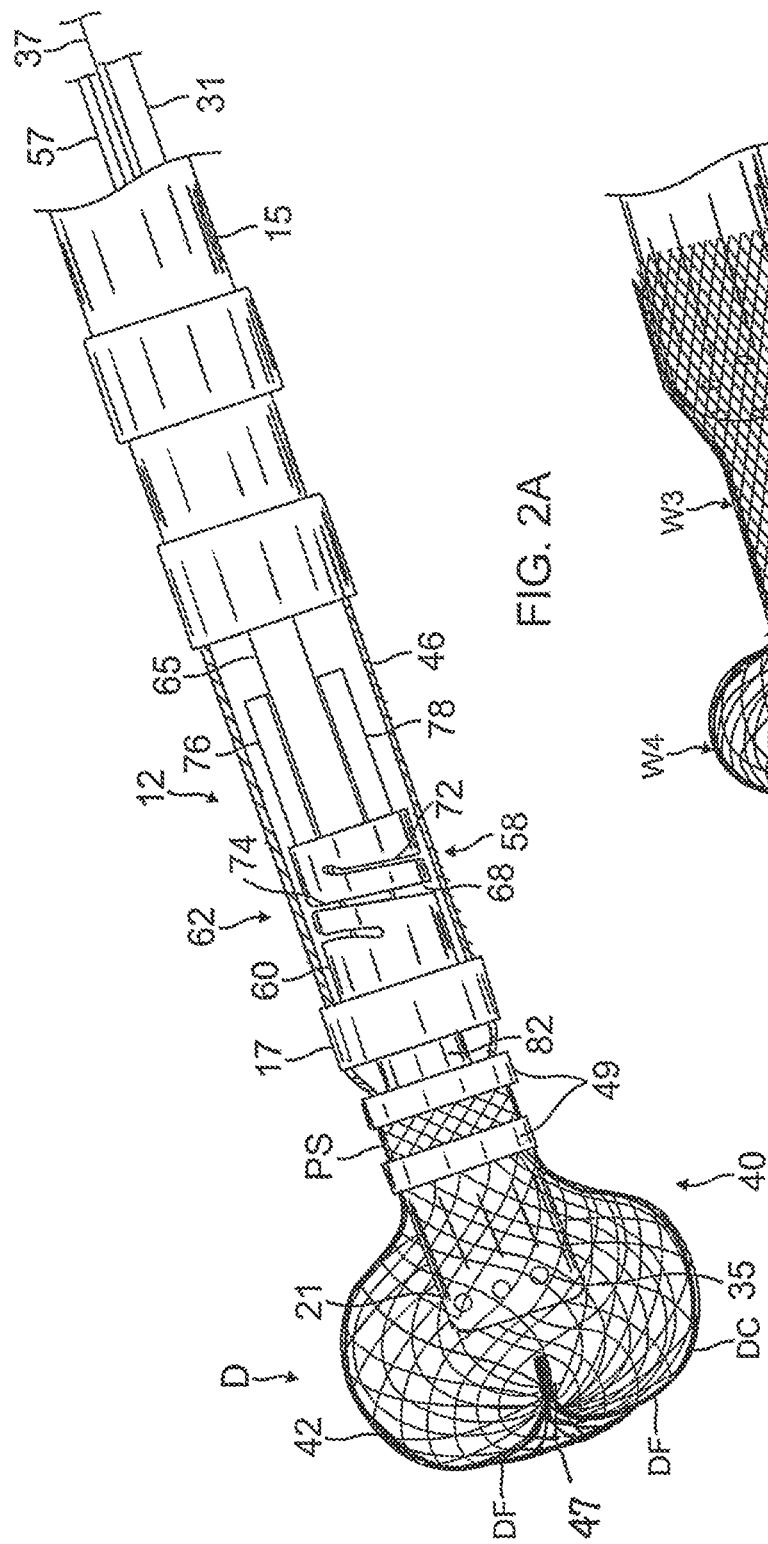
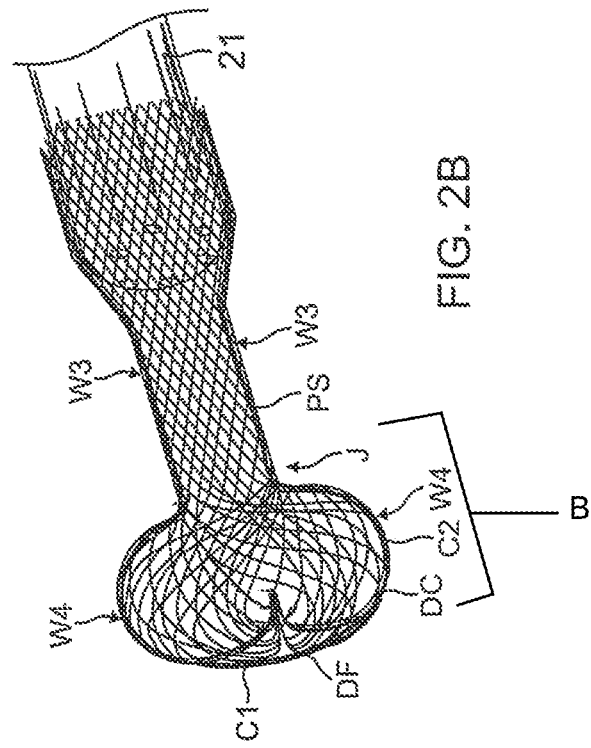
FIG. 2A
FIG. 2B

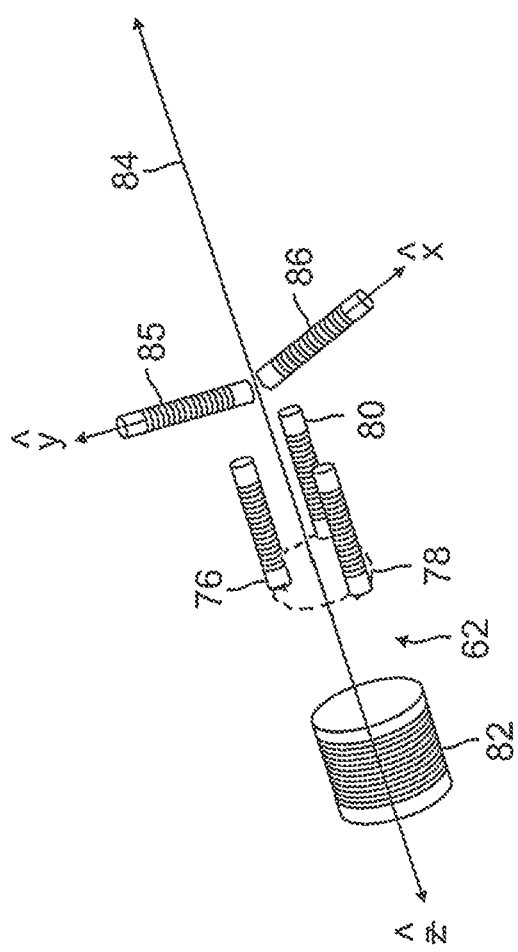
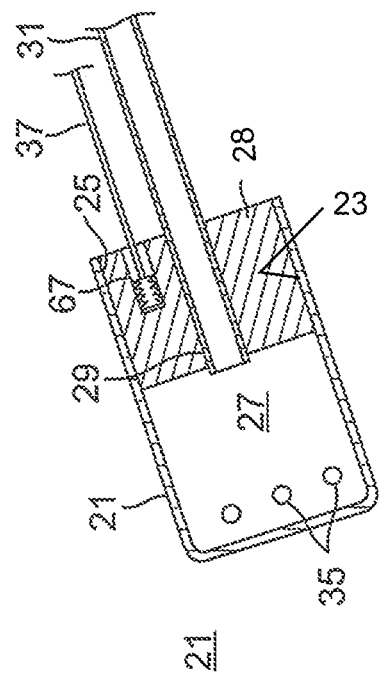
FIG. 3
FIG. 4

CATHETER WITH DEFORMABLE DISTAL ELECTRODE

FIELD OF INVENTION

This invention relates to electrophysiologic (EP) catheters, in particular, deflectable EP catheters for RF ablation.

BACKGROUND

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral vein, and then guided into the chamber of the heart which is of concern. In some medical procedures, energy is imparted to body tissue locally, in a concentrated dose, and it is desirable to cool the treatment area in order to reduce collateral tissue damage. For example, cardiac ablation therapy is used to treat arrhythmias by heating tissue with radio-frequency (RF) electrical energy to create non-conducting lesions in the myocardium. It has been found that cooling the area of the ablation site reduces tissue charring and thrombus formation. Catheters with irrigated distal tips are known as part of integrated ablation system. Typically, a metal catheter tip, which is energized with RF current to ablate the tissue, has a number of irrigation holes, distributed circumferentially around the tip, for irrigation of the treatment site. A pump coupled to the catheter delivers saline solution to the catheter tip, and the solution flows out through the holes during the procedure in order to cool the catheter tip and the tissue.

In certain regions of the heart, for example, in the ventricles where tissue is thicker, the creation of transmural lesions can be challenging. Deep lesions typically require higher RF energy but higher RF energy can lead to undesirable steam pops. Thus, there is a desire to create deeper lesions by increasing electrode/tissue contact area but without increasing the size of the catheter itself.

Catheters with flexible tips are known. U.S. Pat. No. 5,720,719 describes a catheter having a probe end that includes a malleable tube and a flexible tube. U.S. Patent Publication No. 2014/0121657, whose disclosure is incorporated herein by reference, describes a medical probe having a deformable distal end that includes a flexible and porous material. The flexible and porous material may include a conductive material. An electrical conductor can be coupled to the flexible and porous material so as to convey RF energy to the deformable distal end, and the RF energy can be conveyed to tissue by the deformable distal end conveying the RF energy to the tissue. The medical probe may include means for inflating the deformable end which may include conveying a fluid that irrigates the tissue through pores of the deformable distal end. The means for inflating the deformable distal end may include conveying the fluid the fluid so as to generate a mechanical force sufficient to inflate the deformable distal end. A contact area between the deformable distal and the tissue can increase upon pressing the deformable distal end against the tissue.

U.S. Pat. No. 8,249,685 is directed to an apparatus for mapping and/or ablating tissue that includes a braided conductive member that may be inverted to provide a ring shaped surface. When a distal tip of the braided conductive member is retracted within the braided conducive member, the lack of protrusion allows the ring-shaped surface to contact a tissue wall such as a cardiac wall. In an undeployed configuration, the braided conductive member is longitudinally extended, and in a deployed configuration, the distal end of the braided conductive member is retracted to invert the braided conductive member.

The descriptive above is presented as a general overview of related art in this field and should be not be construed as an admission that any of the information it contains constitutes prior art against the present patent application.

SUMMARY OF THE INVENTION

The present invention is directed to a catheter probe configured with a capability to present a larger tissue contact area or "footprint" for larger, deeper lesions, without increasing the french size of the catheter, especially its distal section. In some embodiments, the catheter probe includes a flexible elongated shaft and a distal section having a distal tip end, and an elastically deformable electrode configured to adopt a neutral configuration and a tissue contact configuration. The deformable electrode comprising a hollow porous tube with a distal portion having a closed distal end, and a proximal portion defining an opening to an interior of the tube, where the distal tip end is received in the tube through the opening and the distal section is generally surrounded by tube, with the proximal portion being affixed to an outer surface of the distal section. Advantageously, the closed distal end of the tube is spaced apart from the distal tip end so as to allow the distal portion to deform and expand to provide a larger tissue contact area.

In some embodiments, the distal portion has a preshaped bulbous configuration.

In some embodiments, the preshaped bulbous configuration has a continuous curvature.

In some embodiments, distal portion of the tube has a greater width that is at least about 1.5 times to 3 times or more greater than the width of the proximal portion.

In some embodiments, the tube is porous.

In some embodiments, the tube is constructed of a woven material.

In some embodiments, the tube is constructed of woven, electrically conducting fibers.

In some embodiments, the tube is constructed of a biocompatible elastomeric material.

In some embodiments, the tube is constructed of an electrically-conductive material in conductive connection with an RF tip electrode.

In some embodiments, the catheter probe includes a coupling member between the distal section and the elongated shaft. In more detailed embodiments, the coupling member includes a tubular member configured as a spring joint, wherein the spring joint is configured to be responsive to axial and angular forces acting on the distal section.

In other embodiments, a catheter probe of the present invention includes a flexible elongated shaft and a distal section having a distal tip electrode, and an elastically deformable tube of woven fibers, wherein the deformable tube is configured to adopt (i) a neutral configuration having a preformed bulbous portion with a first width and (ii) a tissue contact configuration wherein the bulbous portion deforms into a second width greater than the first width.

In some embodiments, the bulbous portion is free from contact with the distal tip electrode when the deformable tube is in the neutral configuration, and the bulbous portion is in contact with the distal tip electrode when the deformable tube is in the tissue contact configuration, In some embodiments, the deformable tube has a closed distal end comprising converging fibers and an open end defining an opening receiving the distal tip electrode, and In some embodiments, the deformable tube is electrically connected to an ablation energy source In some embodiments, the bulbous portion has a continuous curvature when the deformable tube is in the neutral configuration and the tissue contact configuration.

In some embodiments, the catheter probe includes a coupling member between the distal section and the elongated shaft, where the coupling member is configured to be responsive to axial and angular forces acting on the distal section.

BRIEF DESCRIPTION OF THE DRAWINGS

These and other features and advantages of the present invention will be better understood by reference to the following detailed description when considered in conjunction with the accompanying drawings wherein:

FIG. 2A is a side view of a catheter probe, including a distal section with a deformable electrode, according to an embodiment of the present invention.

FIG. 2B is a side view of a distal section with a tube and distal tip electrode during assembly.

FIG. 3 is a schematic illustration of a force sensing subsystem and a position sensing subsystem, according to an embodiment of the present invention.

FIG. 4 is a side cross-sectional view of a distal tip electrode, according to an embodiment of the present invention.

DETAILED DESCRIPTION OF THE INVENTION

Figure 1:
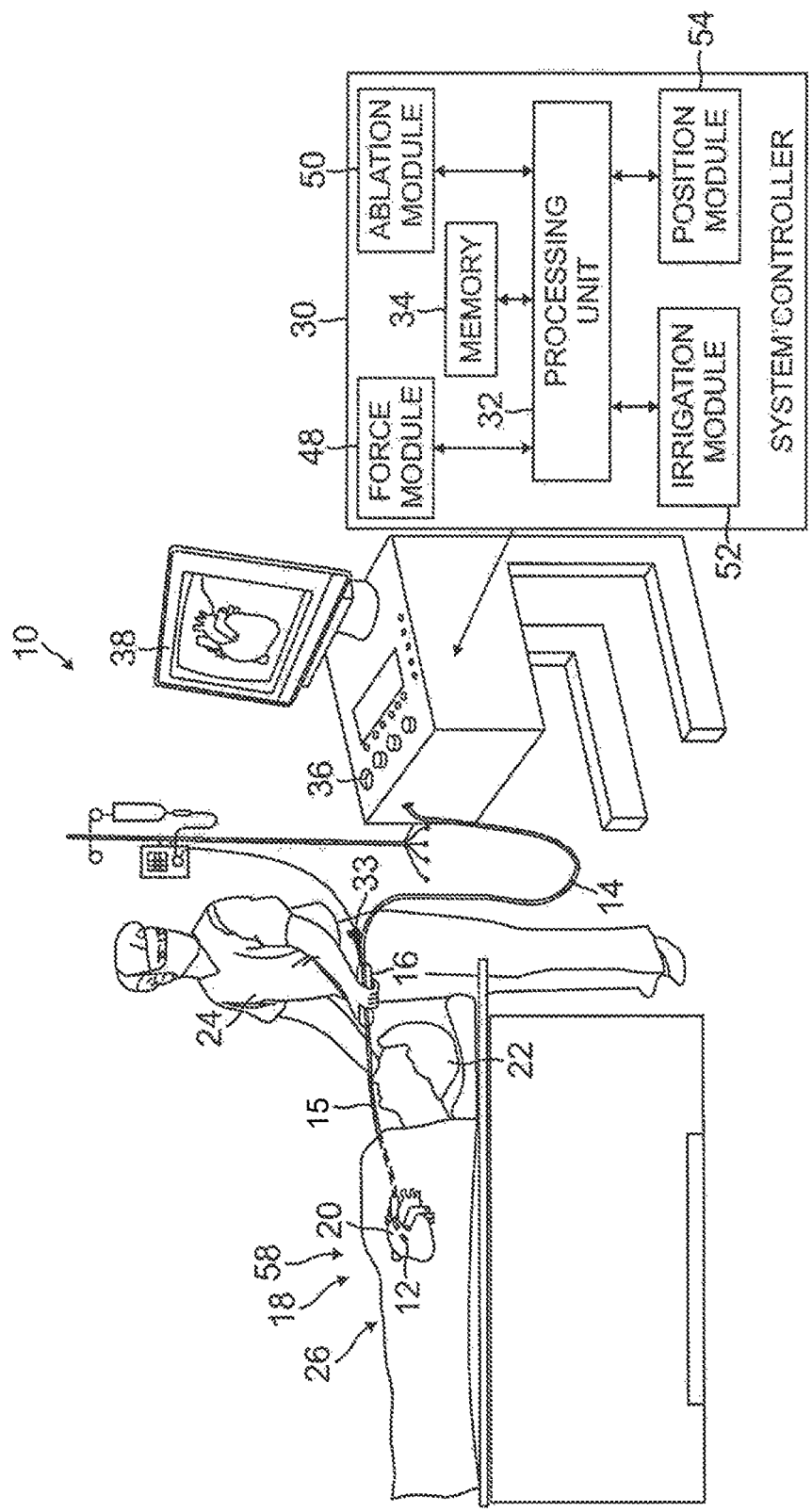
FIG. 1 is a schematic, pictorial illustration of a catheter probe ablating system, according to an embodiment of the present invention.

Reference is now made to FIG. 1, which is a schematic, pictorial illustration of a catheter probe ablating system 10, and to FIG. 2A which illustrates a distal section 12 of a catheter probe 14 used in the system, according to embodiments of the present invention. In system 10, probe 14 comprises an elongated shaft 15 supporting the distal section 12 and the distal section 12 and a portion of the shaft 15 are inserted into a vasculature of a subject 22, for example, a chamber of a heart 20. The probe is used by an operator 24 of system 10, during a procedure which typically includes performing ablation of body tissue 26. The distal section 12 advantageously includes a deformable electrode 40.

In some embodiments, for example, for intracardiac procedure, the shaft 15 and the distal section 12 have a very small outer diameter, typically of the order of 2-3 mm. Therefore, all of the internal components of catheter probe 14, are also made as small and thin as possible and are arranged so as to, as much as possible, avoid damage due to small mechanical strains.

As shown in FIG. 1, the functioning of system 10 is managed by a system controller 30, comprising a processing unit 32 communicating with a memory 34, wherein is stored software for operation of system 10. In some embodiments, the controller 30 is a computer comprising a processing unit, and at least some of the functions of the controller may be performed using custom-designed hardware and software, such as an application specific integrated circuit (ASIC) or a field programmable gate array (FPGA). Controller 30 is typically managed by operator 24 using a pointing device 36 and a graphic user interface (GUI) 38, which enable the operator to set parameters of system 10. GUI 38 typically also displays results of the procedure to the operator.

The software in memory 34 may be downloaded to the controller 30 in electronic form, over a network, for example. Alternatively or additionally, the software may be provided on non-transitory tangible media, such as optical, magnetic, or electronic storage media.

In some embodiments, the controller 30 comprises a force module 48, an RF ablation module 50, an irrigation module 52, and a position module 54. Processing unit 32 uses the force module to generate and measure signals supplied to, and received from, a force sensor 58 in distal end 12 in order to measure the magnitude and direction of the force on the distal end. The operation and construction of force sensor 58 is described in more detail below.

Processing unit 32 uses the RF ablation module 50 to monitor and control ablation parameters such as the level of ablation power applied via electrode(s) on the distal section 12. The ablation module also monitors and controls the duration of the ablation that is provided.

Typically, during ablation, heat is generated in ablation electrodes, as well as in the surrounding region. In order to dissipate the heat and to improve the efficiency of the ablation process, system 10 supplies irrigation fluid to distal end 12. System 10 uses irrigation module 52 to monitor and control irrigation parameters, such as the rate of flow and the temperature of the irrigation fluid, as is described in more detail below.

Processing unit 32 uses position module 54 to monitor the location and orientation of the distal section relative to patient 22. The monitoring may be implemented by any tracking method known in the art, such as one provided in the Carto3® system available from Biosense Webster of Diamond Bar, Calif. Such a system uses radio-frequency (RF) magnetic transmitter and receiver elements external to patient 22 and within distal end 12. Alternatively or additionally, the position and tracking may be implemented by measuring impedances between one or more sensing electrodes 17 on the catheter probe 14, and patch electrodes 18 attached to the skin of patient 22, such as is also provided in the Carto3® system.

As shown in FIG. 2A, distal section 12 is connected to the elongated shaft 15. The distal section includes the force sensor 58. Aspects of a force sensor similar to force sensor 58 are described in U.S. Pat. No. 8,357,152, issued on Jan. 22, 2013 to Govari et al., entitled CATHETER WITH PRESSURE SENSING, and in U.S. Patent Publication No. 2011/0130648, to Beeckler et al., filed Nov. 30, 2009, entitled CATHETER WITH PRESSURE MEASURING TIP, both of whose disclosures are incorporated herein by reference.

FIG. 2A shows a side view of force sensor 58. Sensor 58 comprises a resilient coupling member 60, which forms a spring joint 62. In some embodiments, the coupling member 60 has a hollow tubular form with a central lumen 68 therethough. Although there is no necessity that coupling member 60 be formed of two parts or longitudinal halves, the two part implementation simplifies assembly of elements comprised in the force sensor, as well as of other elements mounted in the distal section 12, into the member 60. Typically, coupling member 60 is formed of a superelastic alloy, such as nickel titanium (Nitinol).

Coupling member 60 typically has one or more helices cut or otherwise formed in the member, so that the member behaves as a spring. In an embodiment described herein, and illustrated in FIGS. 2A and 2C, helices are formed as two intertwined helices, a first cut helix 72 and a second cut helix 74, which are also referred to herein as a double helix. However, coupling member 60 may have any positive integral number of helices, and those having ordinary skill in the art will be able to adapt the present description without undue experimentation to encompass numbers of helices other than two. Alternatively, the coupling member may comprise a coil spring or any other suitable sort of resilient component with similar flexibility and strength characteristics to those generated by the one or more tubular helical cuts, referred to above.

Coupling member 60 is mounted within and covered by sheath 46 (shown as transparent), which is typically formed from flexible plastic material. Coupling member 60 typically has an outer diameter that is approximately equal to the inner diameter of sheath 46. Such a configuration, having the outer diameter of the coupling member to be as large as possible, increases the sensitivity of force sensor 58. In addition, and as explained below, the relatively large diameter of the tubular coupling member, and its relatively thin walls, provide a more spacious lumen 68 enclosed within the coupling member which is used by other elements, described below, in the distal end. The sheath 46 extends the length of the coupling member 60 to provide a fluid tight seal around the hollow tubular form. The sheath 46 may be constructed of any suitable biocompatible material that is flexible and insulating, including CELCON, TEFLON or heat-resistant polyurethane.

When catheter probe 14 is used, for example, in ablating endocardial tissue by delivering RF electrical energy through electrode(s) on the distal section 12, considerable heat is generated in the area of distal end 12. For this reason, it is desirable that sheath 46 comprises a heat-resistant plastic material, such as polyurethane, whose shape and elasticity are not substantially affected by exposure to the heat.

As shown in FIG. 2A and FIG. 3, within force sensor 58, typically within the central lumen 68 of the coupling member 60, a joint sensing assembly, comprising coils 76, 78, 80 and 82, provides accurate reading of any dimensional change in joint 62, including axial displacement and angular deflection of the joint, such was when the distal section 12 is advanced into contact with tissue. These coils are one type of magnetic transducer that may be used in embodiments of the present invention. A "magnetic transducer," in the context of the present patent application and in the claims, means a device that generates a magnetic field in response to an applied electrical current and/or outputs an electrical signal in response to an applied magnetic field. Although the embodiments described herein use coils as magnetic transducers, other types of magnetic transducers may be used in alternative embodiments, as will be apparent to those skilled in the art.

The coils in the sensing assembly are divided between two subassemblies on opposite axial sides of joint 62. One subassembly comprises coil 82, which is driven by a current, via a cable (not shown) from controller 30 and force module 48, to generate a magnetic field. This field is received by a second subassembly, comprising coils 76, 78 and 80, which are located in a section of the distal section 12 that is spaced axially apart from coil 82 across the spring joint 62. The term "axial," as used in the context of the present patent application and in the claims, refers to the direction of a longitudinal axis of symmetry 84 of distal end 12. An axial plane is a plane perpendicular to this longitudinal axis, and an axial section is a portion of the catheter contained between two axial planes. Coil 82 typically has an axis of symmetry generally parallel to and coincident with axis 84.

Coils 76, 78 and 80 are fixed in distal end 12 at different radial locations. (The term "radial" refers to coordinates relative to the axis 84.) Specifically, in this embodiment, coils 76, 78 and 80 are all located in the same axial plane at different azimuthal angles about the catheter axis, and have respective axes of symmetry generally parallel to axis 84. For example, the three coils may be spaced azimuthally 120 degrees apart at the same radial distance from the axis.

Coils 76, 78 and 80 generate electrical signals in response to the magnetic field transmitted by coil 82. These signals are conveyed by a cable 57 (FIG. 2A) extending from the distal section 12, and through the shaft 15 and a control handle 16 to controller 30 which uses force module 48 to process the signals in order to measure the displacement of joint 62 parallel to axis 84, as well as to measure the angular deflection of the joint from the axis. From the measured displacement and deflection, controller 30 is able to evaluate, typically using a previously determined calibration table stored in force module 48, a magnitude and a direction of the force on joint 62.

Controller 30 uses position module 54 to measure the location and orientation of distal end 12. The method of measurement may be by any convenient process known in the art. In one embodiment, magnetic fields generated external to patient 22 create electric signals in elements in the distal section 12, and controller 30 uses the electric signal levels to determine the distal section location and orientation. Alternatively, the magnetic fields may be generated in the distal section 12, and the electrical signals created by the fields may be measured external to patient 22. The elements in distal section 12 that are used to locate the distal section 12 include coils 85 and 86 (FIG. 3) and one of the coil 76, 78 and 80 (in addition to their use as elements of force sensor 58) as orthogonal (x, y, z) position elements housed in the distal section 12.

As shown in FIG. 2A, at or near a distal end of the sheath 46, a ring electrode 17 is mounted on an outer surface of the sheath 46. At or near a distal end of the sheath 46, a distal tip member or electrode 21 has a shell wall 23 and a plug member 28, as shown in FIG. 4. The shell wall 23 has an opening 25 and an interior cavity 27. The plug member 28 has an interference fit with the shell wall in the opening 25 thus sealing the interior cavity 27. The plug member 28 has at least one axial through-hole 29 receiving a distal end of an irrigation tubing 31 for transporting fluid (e.g., saline) from a remote source via a luer hub 33 (FIG. 1) that is in communication with a proximal end of the irrigation tubing 31 at or near the control handle 16. Fluid that is delivered into the interior cavity 27 of the distal tip electrode 21 can cool the electrode 21 before exiting the interior cavity 27 via irrigation apertures 35 formed in the shell wall 23 to outside of the electrode 21 to flush and/or cool surrounding tissue.

The distal tip shell wall 23 and the plug member 28 are constructed of electrically conducting material, for example, platinum, gold, or stainless steel and, in some embodiments, is preferably made of a platinum-iridium alloy (90% platinum/10% iridium). The plug member 28 may be configured with one or more blind holes 67 on its proximal face for receiving one or more components, for example, a distal end of a lead wire 37 for energizing the plug member 28. Proximal of the plug member 28 and distal of the spring joint 62, the coil 82 (FIG. 3) of the force sensing subassembly may be housed in the sheath 46, within the lumen 68 of the coupling member 60. The lead wire 37 and the irrigation tubing 31 pass through a protective tubing 65 that extends through the lumen 68 and further through a lumen of the catheter shaft 15.

Figure 5A:
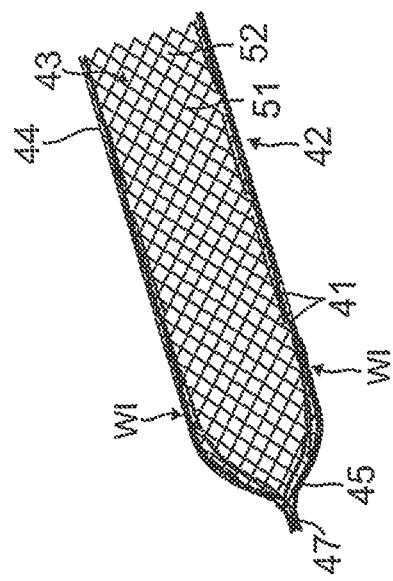
FIG. 5A is a side view of a tube for constructing a deformable electrode, according to an embodiment of the present invention.

FIG. 5A illustrates a woven material suitable for construction of the deformable electrode 40 of the distal section 12. For some applications, a resilient, woven fabric or woven mesh may be advantageous. For enhanced mechanical strength and resilience, the woven material may be woven at least partially from elastic metal fibers, such as strands of Nitinol. The use of a metal-based fabric is also helpful in conducting electrical energy to the intracardiac tissue.

Figure 5C:
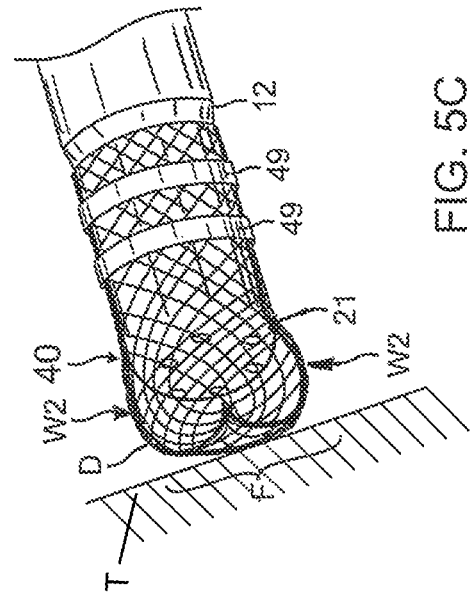
FIG. 5C is a side view of the assembled tube and distal tip electrode of FIG. 5B, wherein the deformable electrode is in contact with tissue.
Figure 5B:
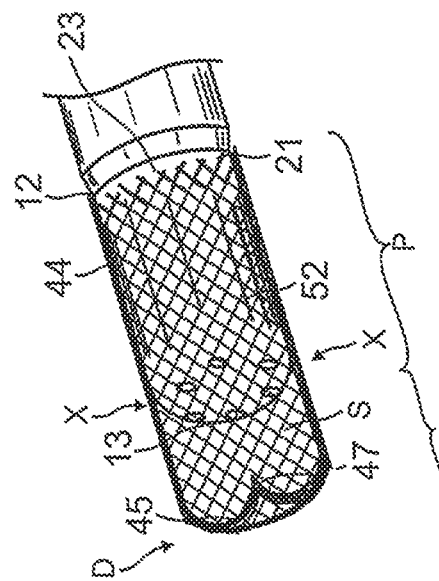
FIG. 5B is a side view of the tube of FIG. 5A, having been inverted, and being assembled with a distal tip electrode.

In some embodiments, the material includes interwoven fibers 41 that are formed as a hollow tube 42, as shown in FIG. 5A, with an outer surface 51 and an inner surface 52 defining a passage 43 between a proximal open end 44, a distal closed end 45 where distal free ends of the fibers 41 are gathered to converge and bunched together into a nub 47, for example, by a other fibers, a fastener, and/or adhesive, to close off the passage 43. With the nub 47 being outside of the passage 43 and pointing distally, as shown in FIG. 5A, the tube 42 is turned inside out and inverted such that the nub 47 is brought in the passage 43 and points proximally, and the inner surface 52 faces outwardly to present a smooth and atraumatic distal end surface, as shown in FIG. 5B. The tube 42 is then slipped onto or otherwise mounted over the distal section 12 with a distal tip end 13 being inserted through the proximal open end 44. The distal section 12 is advanced to a location X that is proximal of the distal closed end 45 of the tube 42 such that there is volume space gap S between the distal closed end 45 of the tube 42 and distal tip end 13 of the distal section 12, when the tube 42 is in its neutral configuration free from external deformation force. As such, the tube 42 in its neutral configuration has a first or distal portion D free from contact with the distal tip electrode 21, and a second or proximal portion P generally in circumferential contact with the distal tip electrode 21. The proximal open end 44 of the tube 42 extends around the proximal end of shell wall 23 of the distal tip electrode 21 and is wrapped around and secured to the shell wall 23 by one or more bands 49 (see FIG. 2A). Affixed in this manner, the tube 42 is in direct, electrically-conductive contact with shell wall 23 such that energization of the shell wall 23 also energizes the tube 42. Moreover, because the tube 42 is resilient, its distal portion D readily compresses down to a size not greater than the width or french size of the distal tip electrode 21 and distal tip section 12 when the catheter is inserted into the patient's vasculature, for example, via a guiding sheath (not shown), and readily resumes its neutral configuration when deployed from the guiding sheath.

In some embodiments, the tube 42 may have a uniformly cylindrical configuration, as shown in FIG. 5A and FIG. 5B. The tube 42, in its neutral configuration, has a generally uniform width W1 along its length, the width W1 being equal to or greater than the width of the distal tip electrode 21 such that the electrode 21 may be readily inserted into the tube 42 without significantly stretching the weave of the underlying material. Moreover, as shown in FIG. 5C, the distal portion D of the tube 42 expands and bulges radially from its neutral configuration to a width W2>W1 when distal face F of the tube 42 comes in contact with tissue upon advancement of the distal section 12 and further when the distal tip electrode 21 abuts or contacts tissue surface T. With such radial expansion, the distal portion D of the tube 42 enables the deformable electrode 40 to provide a larger contact surface area or footprint F by which the tissue can be ablated compared to that of the distal tip electrode 21 alone.

In other embodiments, the tube 42 may have a neutral configuration having a mushroom shape, as shown in FIG. 2B, with a distal cap portion DC and a proximal stem portion PS. The proximal stem portion PS is generally straight, with a generally uniform width W3 along its length where the width W3 may be generally equal to or less than the width of the distal tip electrode 21. The distal cap portion DC of the tube 42 has a distal face DF that is generally flat or having a lesser curvature C1, and a bulbous portion B having a greater curvature C2 that is continuous and thus free of any corners or sharp transitions. A width W4 of the bulbous portion B is at least about 1.5 times the width W3 of the stem portion PS. When mounted on the distal section 12, the proximal stem portion PS is generally in circumferential contact with the distal tip electrode 21 and the distal cap portion DC is free from contact with the distal tip electrode 21, as shown in FIG. 2A.

Figure 2C:
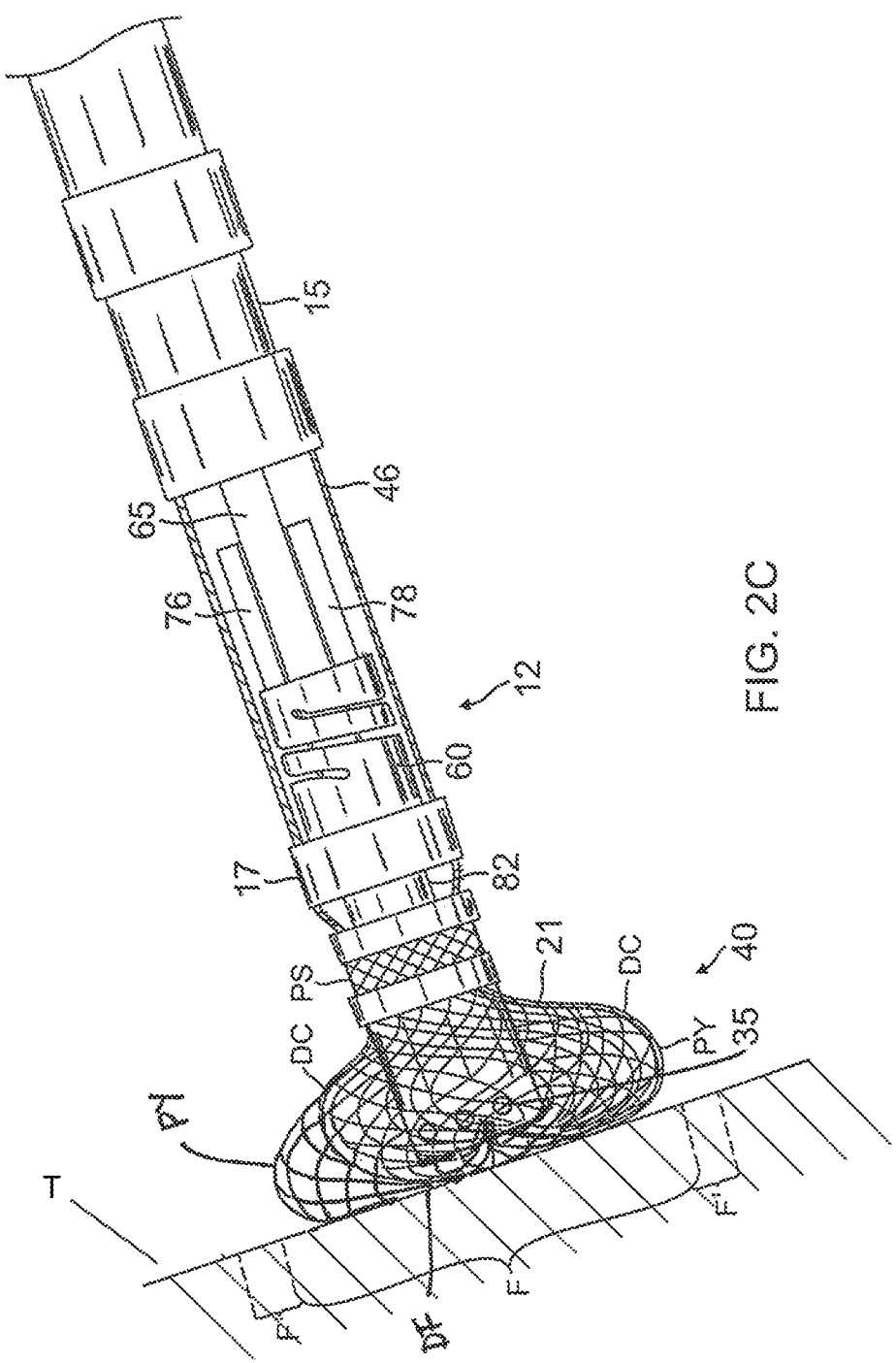
FIG. 2C is a side view of the catheter probe of FIG. 2A, wherein the deformable electrode is in contact with tissue.

When the distal face DF of the tube 42 comes in contact with tissue T upon advancement of the distal section 12 toward the tissue, as shown in FIG. 2C, the distal cap DC including the bulbous portion B becomes more flattened and spreads out, expanding radially for a significantly enlarged contact surface area or footprint F compared to that of the distal tip electrode 21. With the distal cap DC and its bulbous portion B having a continuous curvature with no sharp angles or corners, the distal cap DC and bulbous portion B can readily keep its overall shape during expansion without any kinking or undesirable deformation.

For any embodiments of the present invention, the tissue contact surface area F can be increased by pivoting the distal section 12 about an axis perpendicular to the contact surface area (in sweeping out a conical volume). In this manner, peripheral portions PY of the bulbous portion B can also be brought into contact with additional tissue surface F'.

In operation, the distal portion D of the tube 42 of the embodiments herein can be inflated and irrigated by fluid, e.g., a saline solution or any other type of suitable irrigation fluid), which the irrigation module 52 pumps through the irrigation tubing 31 to deliver the saline to the distal tip electrode 21 where it exits through the irrigation apertures 35, thereby generating a mechanical force sufficient to inflate distal portion D of the tube 42. While the distal portion D of the tube 42 is inflated and pressed against endocardial tissue T, the distal portion may better conform to the endocardial tissue T, as shown in FIG. 2C.

When deformable electrode 40 is conductive, e.g., by comprising suitable metal strands or a conductive polymer, ablation module 50 can convey RF energy to the deformable electrode 40 via the lead wire 37, and the deformable electrode 40 conducts the energy to the tissue. Alternatively or additionally, the lead wire 37 may apply the RF energy to conductive fluid (e.g., saline) delivered into the distal tip electrode 21, in which case the conductive solution may conduct the RF energy through deformable electrode 40 to the endocardial tissue.

Figure 6:
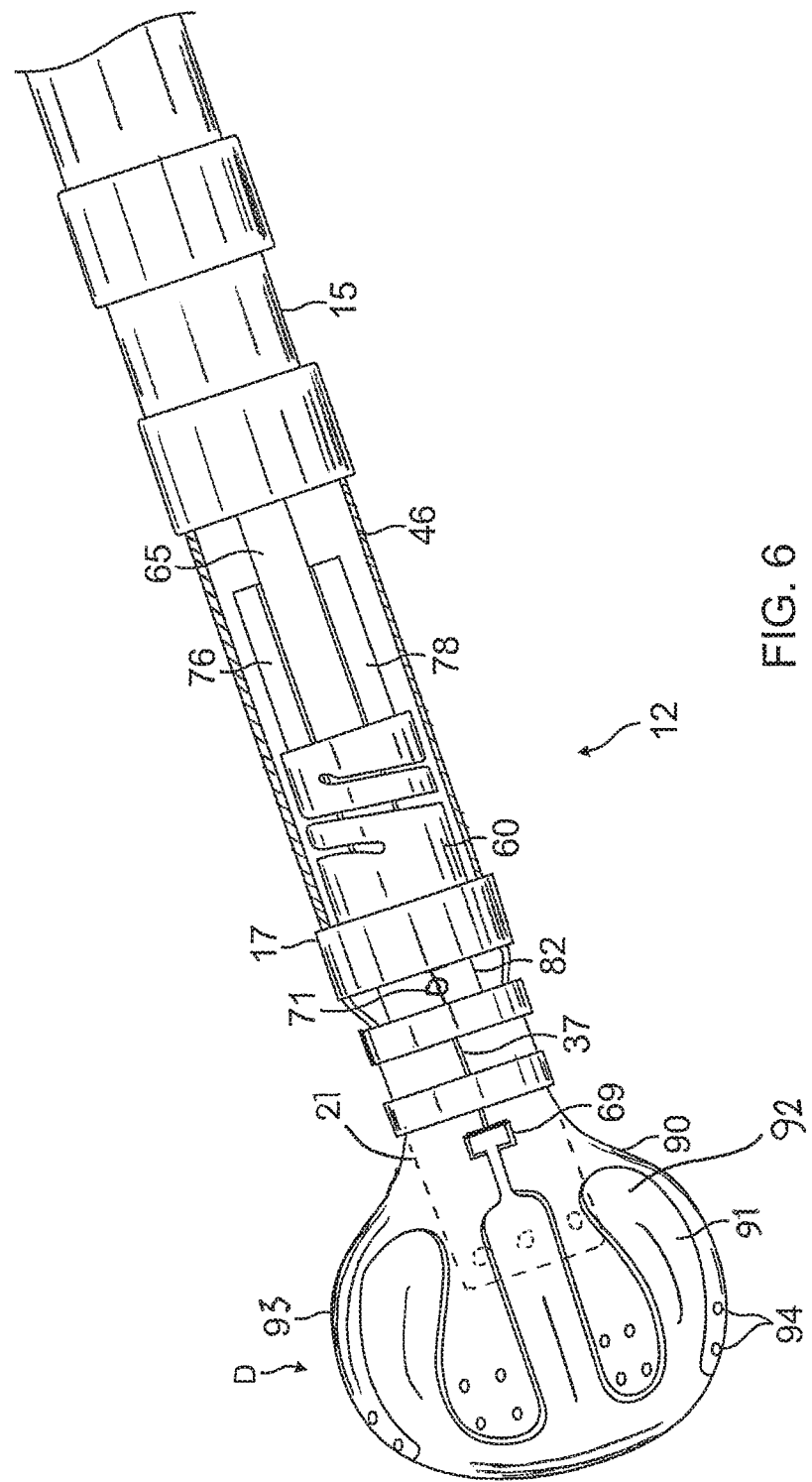
FIG. 6 is a side view of a catheter probe, including a distal section with a deformable electrode, according to another embodiment of the present invention.

In other embodiments, as shown in FIG. 6, the deformable electrode 40 may comprise an irrigated balloon tube 90 comprising a biocompatible flexible and elastomeric substrate 91 having an outer surface 92 on which one or more conductive members or surface electrodes 93 are painted or otherwise applied, for example, as printed circuits, sputter coatings, etc. It is understood that the substrate 91 and balloon member 90 may assume any one or more of the applicable characteristics described above and/or illustrated herein for the tube 42. Where the substrate 91 is not woven or otherwise porous, irrigation ports 94 may be formed in the substrate 91 for fluid transported into the interior cavity of the 27 of the balloon member 90 to exit the balloon member 90.

Figure 7:
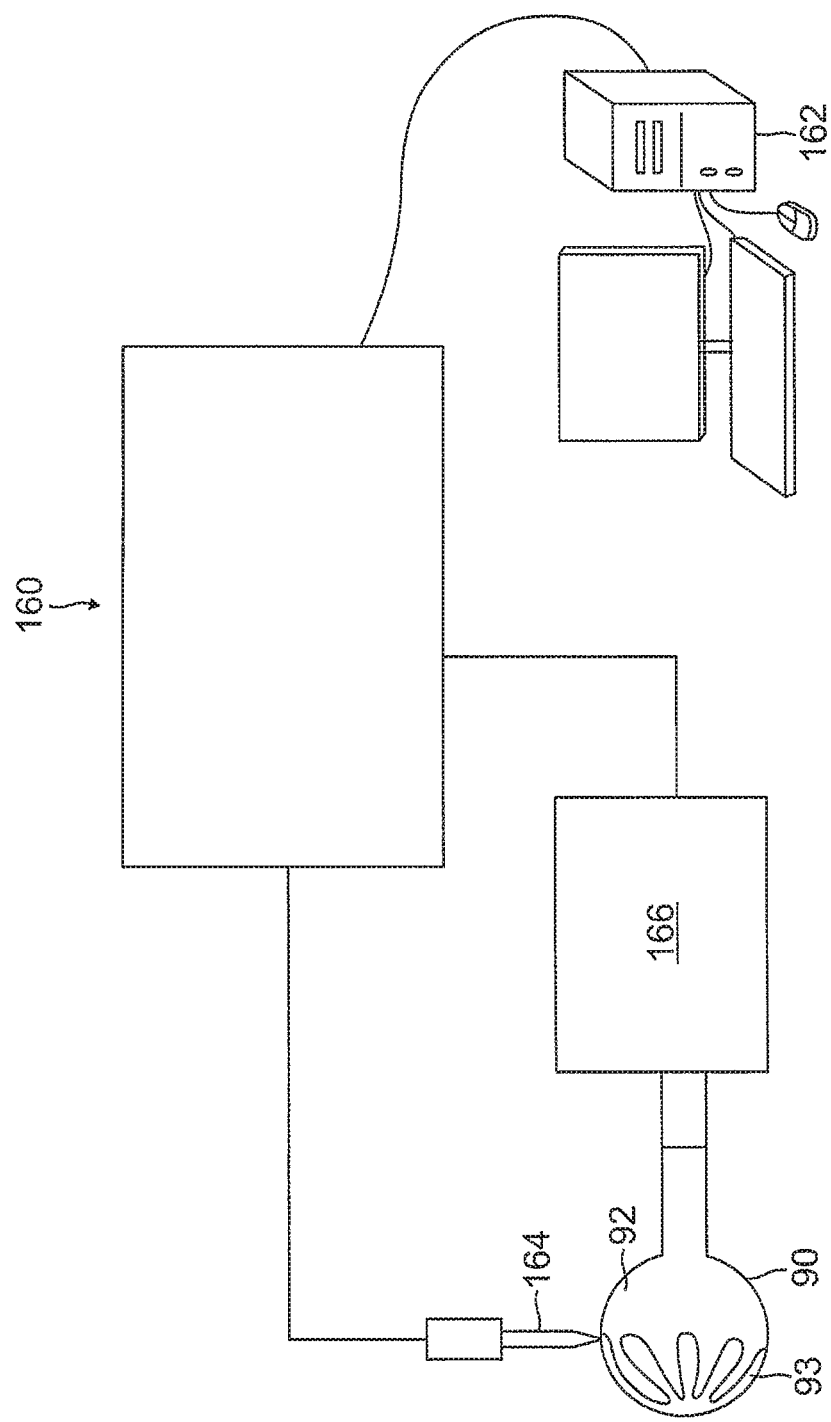
FIG. 7 is a schematic illustration of a positive displacement dispensing system, as used in the present invention, according to one embodiment.

In certain embodiments, a conductive material forming the surface electrodes 93 is applied by a micropen or positive displacement dispensing system, as understood by one of ordinary skill in the art. A micropen can dispense a controllable volume of paste per time, which enables control of thickness by varying print volume, paste concentration, and write speed. As shown in FIG. 7, a positive displacement dispensing system 160 includes a pen tip 164 that is kept substantially perpendicular to the surface of the substrate or underlying material. Such a system is disclosed in U.S. Pat. No. 9,289,141, titled "Apparatus and Methods for the Measurement of Cardiac Output." Positive displacement dispensing technologies and direct-write deposition tools including aerosol jets and automated syringes are available under the mark MICROPEN by MicroPen Technologies and Ohmcraft, Inc., both of Honeoye Falls, N.Y.

As shown in FIG. 7, the balloon member 90 is at least partially inflated prior to printing the electrodes 93 on its outer surface 92. A processing system, such as a computer 162, generates a contour image map showing the contours of the balloon member 90. Information from the contour map obtained above is provided to the positive displacement dispensing system 160 capable of responding to the contour map by altering one or more printing dimensions. In some embodiments, the positive displacement dispensing system 160 contains a writing head 164 (such as a pen tip) and a substrate stage 166 capable of moving the balloon member 93 in at least three independent dimensions. The writing head is 164 capable of movement relative to the substrate stage 166. The writing head 164 applies to the substrate any liquid or semi-solid materials, and the conductive material used to form the electrode(s) 93.

The writing head 164 is mounted on an axis capable of moving in one dimension only, shown in FIG. 7 as the y-axis. In contrast, the substrate stage 166 capable of moving in at least three independent dimensions: the x-axis, .phi. (clockwise or counter-clockwise rotation along the z-axis, and .theta. (clockwise or counter-clockwise rotation along the x-axis). In certain embodiments, the substrate stage 166 is capable of moving in a fourth independent direction, shown in FIG. 7 as the y-axis.

The surface electrodes 93 may assume any variety of patterns on the balloon member 90. One or more solder pads 69 (FIG. 6) may be provided to electrically connect internal lead wires 37 and the surface electrodes 93. One or more lead wires 37 may transition from inside the sheath 46 to outside via aperture(s) 71 formed in the sheath 46 to connect with the solder pad(s) 69. In other embodiments, the electrodes 93 are connected to the tip electrode 21 by lead wires to conduct RF energy. The lead wires may run along the outer surface of the balloon member 90 to reach the tip electrode 21, or they may run through the interior of the balloon member to reach the tip electrode 21.

Figure 8A:
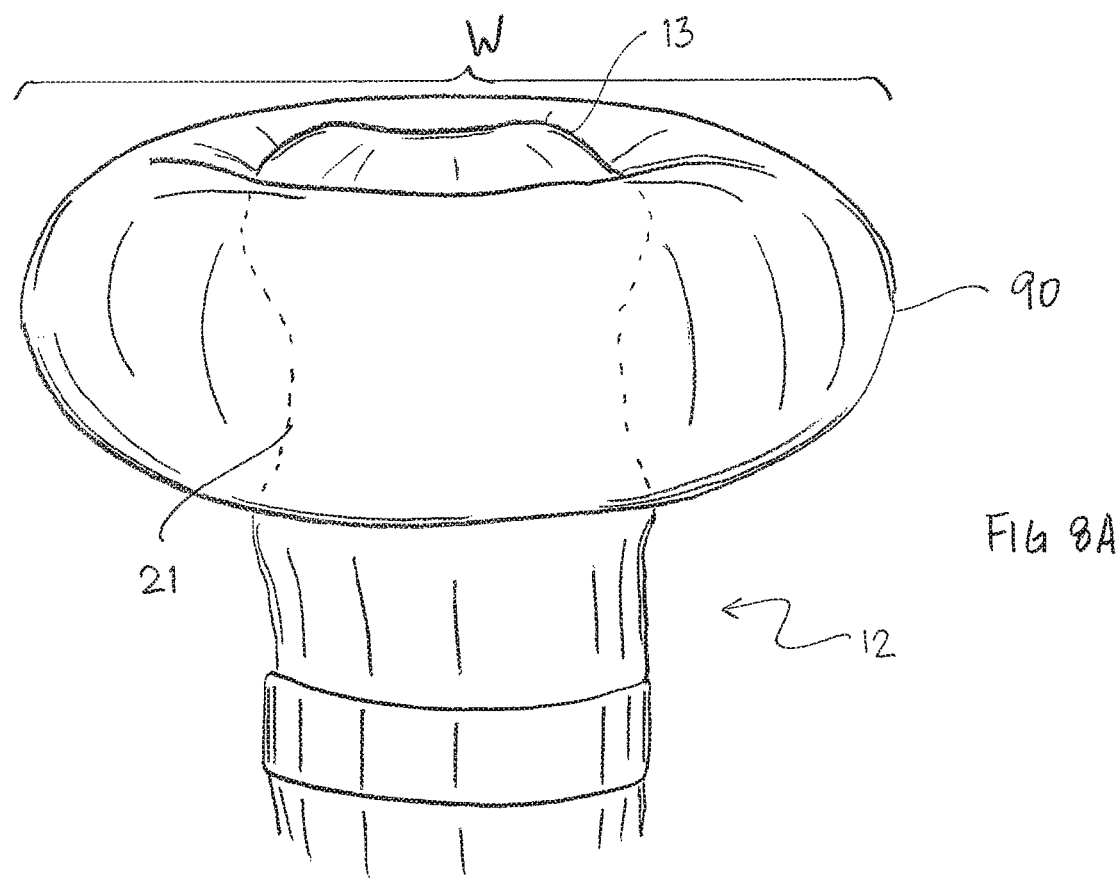
FIG. 8A is a side view of a catheter probe, including a balloon member, according to another embodiment of the present invention.
Figure 8B:
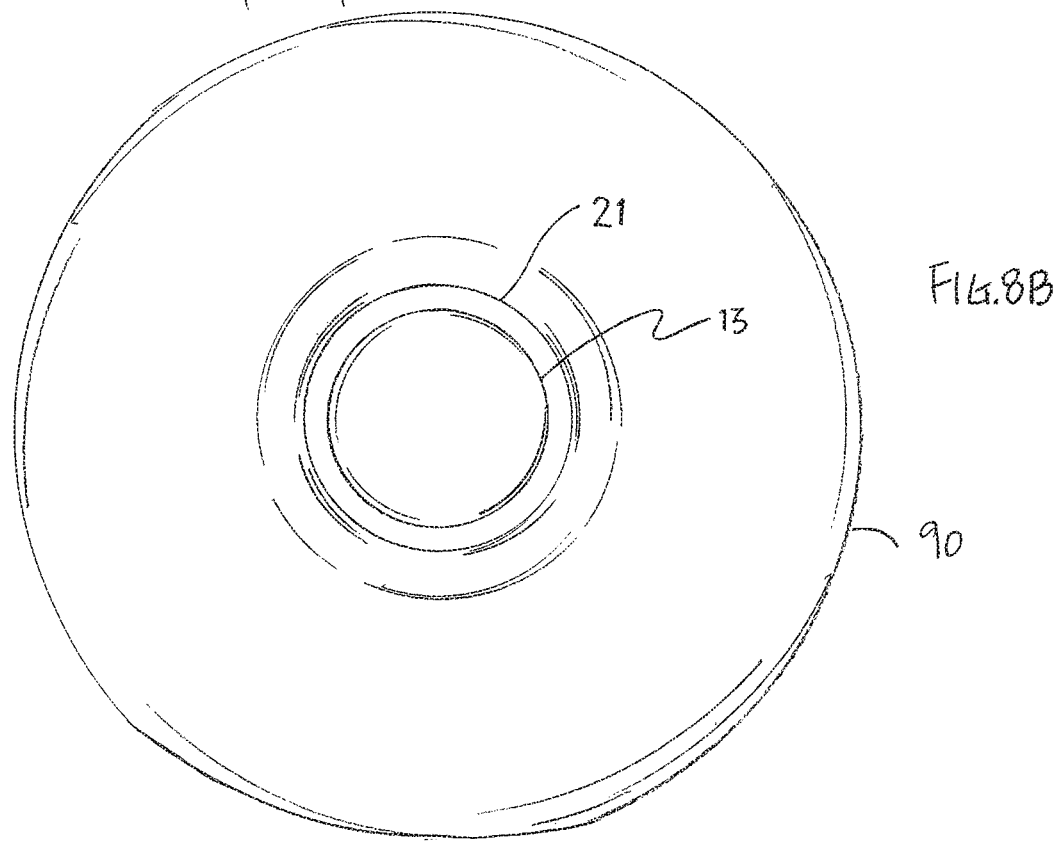
FIG. 8B is an end view of the catheter probe of FIG. 8A.

In some embodiments, the balloon member 90 is constructed of a conductive polymer. In some embodiments, the balloon member 90 has a bulbous or donut shape, defined as a toroidal configuration having a generally circular cross-section, and a center opening through which the distal tip electrode 21 extends, as shown in FIG. 8A and FIG. 8B. In some embodiments, the balloon member 90 has a width W ranging between about 4.0 mm and 5.1 mm. As shown in FIG. 8B, the balloon member 90, when inflated, presents a distal surface in the shape of a ring for contact with tissue surface.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale, and any feature or combinations of features described in some embodiments may be incorporated into any other embodiments or combined with any other feature(s) of another embodiment, as desired or needed. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter probe, comprising:
a flexible elongated shaft;
a distal section at a distal end of the flexible elongated shaft, the distal section having a distal tip end, and an elastically deformable electrode configured to adopt a neutral configuration and a tissue contact configuration, the deformable electrode comprising a hollow porous tube that is porous along its entire length and has a distal portion having a closed distal end, and a proximal portion defining an opening to an interior of the hollow porous tube, the distal tip end being received in the hollow porous tube through the opening, the distal section being generally surrounded by the hollow porous tube and the hollow porous tube being affixed to an outer surface of the distal section, the hollow porous tube comprising a plurality of interwoven fibers having free distal ends that converge into a nub situated within an inner passage of the hollow porous tube and extending proximally from the closed distal end;
wherein the closed distal end of the distal portion of the hollow porous tube is spaced apart from the distal tip end, and the distal portion of the hollow porous tube has a lesser width (W1) when the deformable electrode is in the neutral configuration, and
wherein the distal portion of the hollow porous tube has a greater width (W2) when the deformable electrode is in the tissue contact configuration.

2. The catheter probe of claim 1, wherein the distal portion of the hollow porous tube has a preshaped bulbous configuration.

3. The catheter probe of claim 2, wherein the preshaped bulbous configuration has a continuous curvature.

4. The catheter probe of claim 1, wherein the greater width (W2) is at least about 1.5 times greater than the lesser width (W1).

5. The catheter probe of claim 1, wherein the plurality of interwoven fibers includes a plurality of interwoven, electrically conducting fibers.

6. The catheter probe of claim 1, wherein the neutral configuration comprises a mushroom shape.

7. The catheter probe of claim 1, wherein the neutral configuration comprises a mushroom shape having a distal cap portion with a greater width (W4) and a proximal stem portion with a lesser width (W3).

8. The catheter probe of claim 7, wherein the width (W3) of the proximal stem portion is generally uniform along a length of the proximal stem portion.

9. The catheter probe of claim 7, wherein the distal cap portion comprises a distal face having a lesser curvature (C1) and a bulbous portion having a greater curvature (C2).

10. The catheter probe of claim 9, wherein the distal face is generally flat.

11. The catheter probe of claim 9, wherein the curvature (C2) of the bulbous portion is generally continuous.

12. The catheter probe of claim 7, wherein the width (W4) of the distal cap portion is at least 1.5 times the width (W3) of the proximal stem portion.

13. The catheter probe of claim 7, wherein in the neutral configuration, the proximal stem portion is in generally circumferential contact with the distal tip end, and the distal cap portion is generally free from contact with the distal tip end.

14. A catheter probe, comprising:
a flexible elongated shaft;
a distal section distal of the flexible elongated shaft and having a distal tip electrode, and an elastically deformable porous tube, wherein the deformable porous tube is porous along its entire length and is configured to adopt (i) a neutral configuration having a preformed bulbous portion with a first width and (ii) a tissue contact configuration wherein the bulbous portion deforms into a second width greater than the first width;
wherein the bulbous portion is free from contact with the distal tip electrode when the deformable porous tube is in the neutral configuration, and the bulbous portion is in contact with the distal tip electrode when the deformable porous tube is in the tissue contact configuration,
wherein the deformable porous tube has a closed distal end and comprises a plurality of interwoven fibers having free distal ends that converge into a nub situated within an inner passage of the deformable porous tube and extending proximally from the closed distal end, the deformable porous tube having an open end defining an opening receiving the distal tip electrode, the deformable porous tube being affixed to an outer surface of the distal section, and
wherein the deformable porous tube is electrically connected to an ablation energy source.

15. The catheter probe of claim 14, wherein the bulbous portion has a continuous curvature when the deformable porous tube is in the neutral configuration and the tissue contact configuration.

16. The catheter probe of claim 14, wherein the plurality of interwoven fibers includes a plurality of interwoven, electrically conducting fibers.

* * * * *